United States Patent [19]
Ankner et al.

[11] Patent Number: 4,689,331
[45] Date of Patent: Aug. 25, 1987

[54] SUBSTITUTED 2-PYRIDINYL BENZIMIDAZOLES, AND THEIR USE FOR INHIBITING GASTRIC ACID SECRETION

[75] Inventors: Kjell F. Ankner, Mölnlycke; Arne E. Brändström, Göteborg; Per L. Lindberg, Askim; Mats P. Nordberg, Göteborg; Björn M. G. Wallmark, Mölnlycke, all of Sweden

[73] Assignee: Aktiebolaget Hassle, Molndal, Sweden

[21] Appl. No.: 788,768

[22] Filed: Oct. 18, 1985

[30] Foreign Application Priority Data

Nov. 8, 1984 [SE] Sweden ................... 8405588

[51] Int. Cl.⁴ ............... C07D 401/04; A61K 31/44
[52] U.S. Cl. ................................. 514/338; 514/333; 546/271; 546/256
[58] Field of Search .............. 546/271, 256; 514/338, 514/333

[56] References Cited

U.S. PATENT DOCUMENTS

| 4,097,603 | 6/1978 | Robert | 514/530 |
| 4,182,776 | 1/1980 | Albright et al. | 514/567 |
| 4,327,102 | 4/1982 | Crossley | 514/277 |

FOREIGN PATENT DOCUMENTS

| 0005129 | 10/1979 | European Pat. Off. |
| 51371 | 5/1982 | European Pat. Off. |
| 80602 | 10/1982 | European Pat. Off. |
| 2754299 | 4/1977 | Fed. Rep. of Germany |
| 2457127 | 6/1978 | Fed. Rep. of Germany |
| 2038825 | 7/1980 | United Kingdom |

Primary Examiner—Jane T. Fan
Attorney, Agent, or Firm—Brumbaugh, Graves, Donohue & Raymond

[57] ABSTRACT

Novel compounds of the formula I

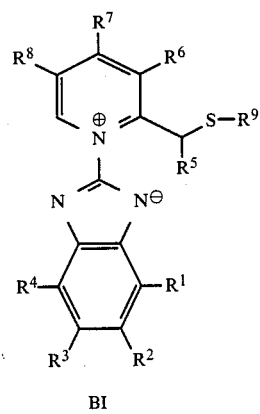

and its salts; process for the preparation thereof, pharmaceutical compositions containing such compounds and their use in medicine to affect gastric acid secretion and provide gastrointestinal cytoprotection.

10 Claims, No Drawings

SUBSTITUTED 2-PYRIDINYL BENZIMIDAZOLES, AND THEIR USE FOR INHIBITING GASTRIC ACID SECRETION

FIELD OF THE INVENTION

The present invention is related to new benzimidazole derivatives having valuable therapeutic properties especially in affecting gastric acid secretion and providing gastrointestinal cytoprotective effect in mammals, including man, as well as processes for the preparation of the new compounds, pharmaceutical compositions comprising them and a method of affecting gastric acid secretion and providing gastrointestinal cytoprotective effect when using them.

BACKGROUND OF THE INVENTION

In several documents e.g. No. EP-A1-005 129, No. GB-A-20 38 825, U.S. Pat. No. 4,327,102, U.S. Pat. No. 4,182,766 and No. EP-A-80 602 heterocyclic compounds active as inhibitors of gastric acid secretion have been described. Two of these documents namely No. EP-A1-1 0 005 129 and No. EP-A-80 602 describe substituted [[(2-pyridinyl)-methyl]-sulfinyl]-1H-benzimidazoles and also in U.S. Pat. No. 4,097,603 such compounds and their thioanalogoues have been described. According to the last mentioned document the compounds are known as cytoprotective agents. Because of their antisecretory effect the known compounds may be used in the treatment of gastrointestinal diseases, e.g. peptic ulcer.

OUTLINE OF THE INVENTION

According to the present invention it has now surprisingly been found that a new type of substituted benzimidazoles, namely compounds of the general formula

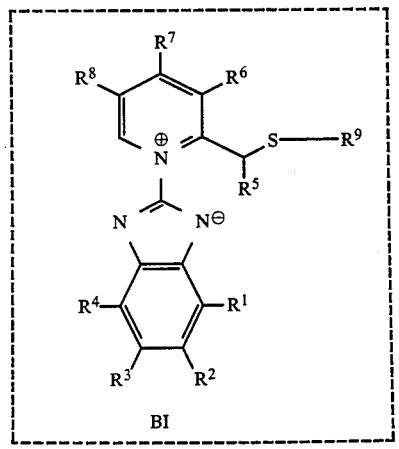

wherein $R^1$, $R^2$, $R^3$ and $R^4$ are the same or different and are hydrogen, an alkyl, cycloalkyl, alkoxy, alkoxyalkyl, alkoxyalkoxy, halogen, —CN, —CF$_3$, —NO$_2$, —COR$^{12}$, alkylthio, alkylsulfinyl, aryl, arylalkyl, aryloxy or arylalkoxy group, or wherein $R^1$ and $R^2$, $R^2$ and $R^3$ or $R^3$ and $R^4$ together with the adjacent carbon atoms in the benzimidazole ring form one or more 5-, 6- or 7-membered rings, which each may be saturated or unsaturated and may contain 0–3 hetero atoms selected from N, S and O, and whereby each ring may be optionally substituted with 1–4 substituents selected from alkyl groups with 1–3 carbon atoms, or two or four of the mentioned substituents together form one or two oxo groups

whereby if $R^1$ and $R^2$, $R^2$ and $R^3$ or $R^3$ and $R^4$ together with the adjacent carbon atoms in the benzimidazole ring form two rings these rings may be condensed with each other; $R^5$, $R^6$ and $R^8$ are the same or different and are selected from hydrogen and alkyl; $R^7$ is hydrogen, an alkyl, alkoxy, aryl, arylalkyl, aryloxy, arylalkoxy, alkenyloxy or alkynyloxy group; or $R^6$ and $R^7$, or $R^7$ and $R^8$ together with the adjacent carbon atoms in the pyridine ring form a 5- or 6-membered, saturated or unsaturated ring, which may optionally contain an oxygen or an optionally alkylated nitrogen atom; $R^9$ is —CN, —SO$_2$H, —SO$_2^\ominus$, —S—A—R$^{10}$, —S—R$^{11}$,

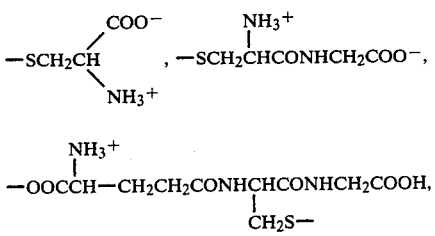

or a group —BI (which is the part of the structure within broken lines as defined in formula I); A is an alkylene or cycloalkylene group; $R^{10}$ is a hydrogen, a —CN, —CF$_3$, —NO$_2$, —COR$^{13}$, —NR$_2^4$, —OR$^{14}$, —SR$^{14}$,

—NHCOR$^{15}$, —OCOR$^{15}$, —SCOR$^{15}$, aryl, arylalkyl, aryloxy or arylalkoxy group; $R^{11}$ is an aryl group which may be optionally substituted by one or more substituents selected from alkyl, alkoxy, halogen, —CN, —CF$_3$, —NO$_2$ and —COR$^{13}$; $R^{12}$ and $R^{15}$ are the same or different and selected from alkyl, aryl, aryloxy and alkoxy; $R^{13}$ is selected from alkyl, aryl, aryloxy, alkoxy and hydroxy; and $R^{14}$ is hydrogen or an alkyl group, as well as pharmaceutically acceptable acid addition salts (IA) thereof and in applicable cases pharmaceutically acceptable alkaline salts thereof (e.g. when $R^9$ is S—CH$_2$CH$_2$COOH) are effective as gastrointestinal cytoprotectives and as inhibitors of gastric acid secretion in mammals and man.

The group alkyl in the definitions of $R^1$, $R^2$, $R^3$, $R^4$, $R^5$, $R^6$, $R^7$, $R^8$, $R^{11}$, $R^{12}$, $R^{13}$, $R^{14}$ and $R^{15}$ is preferably a lower alkyl group having 1–7 carbon atoms, especially preferred 1–4 carbon atoms, e.g. methyl, ethyl, n-propyl, isopropyl, n-butyl or isobutyl.

The group alkoxy in the definitions of $R^1$, $R^2$, $R^3$, $R^4$, $R^7$, $R^{11}$, $R^{12}$, $R^{13}$ and $R^{15}$ is preferably a lower alkoxy group having 1–7 carbon atoms, especially preferred 1–3 carbon atoms, e.g. methoxy, ethoxy, n-propoxy or isopropoxy.

Halogen in the definitions of $R^1$, $R^2$, $R^3$, $R^4$ and $R^{11}$ is preferably chloro, bromo, fluoro or iodo.

In $R^1$, $R^2$, $R^3$ and $R^4$ representing alkylthio or alkylsulfinyl is the alkyl preferably a lower alkyl having 1–7 carbon atoms, especially preferred 1-4 carbon atoms, e.g. methylthio, methylsulfinyl, ethylthio, ethylsulfinyl, isopropylthio, n-butylsulfinyl or isobutylthio.

$R^1$, $R^2$, $R^3$, $R^4$, $R^7$, $R^{10}$, $R^{11}$, $R^{12}$, $R^{13}$ and $R^{15}$ representing an aryl group have preferably up to 10 carbon atoms, especially preferred up to 6 carbon atoms, e.g. a phenyl group.

$R^1$, $R^2$, $R^3$, $R^4$, $R^7$, $R^{10}$, $R^{12}$, $R^{13}$ and $R^{14}$ representing an aryloxy group have preferably up to 10 carbon atoms, especially preferred up to 6 carbon atoms, e.g. a phenoxy group.

$R^1$, $R^2$, $R^3$, $R^4$, $R^7$ and $R^{10}$ representing an arylalkyl or arylalkoxy group have preferably up to 10 carbon atoms in the aryl group and 1-7 carbon atoms in the alkyl group or alkoxy group, respectively, especially preferred are 6 carbon atoms in the aryl group and 1-3 carbon atoms in the alkyl group or alkoxy group, respectively, e.g. phenylmethyl, phenylethyl, phenylmethoxy, phenylethoxy, phenylpropyl and phenylisopropoxy.

$R^1$, $R^2$, $R^3$ and $R^4$ representing an cycloalkyl group have preferably 3-7 carbon atoms, especially preferred 5-6 carbon atoms, e.g. cyclopentyl, cyclohexyl and methylcyclopentyl.

$R^1$, $R^2$, $R^3$ and $R^4$ representing an alkoxyalkyl or alkoxyalkoxy group have preferably 1-7 carbon atoms in the alkoxy group or groups and alkyl group, respectively, especially preferred 1-3 carbon atoms in the alkoxy group or groups and the alkyl group, respectively, e.g. methoxyethyl, methoxypropyl, ethoxyethyl, propoxyethyl, methoxyethoxy, methoxypropoxy, ethoxyethoxy and propoxyethoxy.

$R^7$ representing an alkenyloxy or alkynyloxy group has preferably 2-7 carbon atoms, especially preferred 3-4 carbon atoms, e.g. allyloxy, propargyloxy, 2-butenyloxy and 2-butynyloxy.

Illustrative examples of ring structures formed by $R^1$ and $R^2$, $R^2$ and $R^3$, $R^3$ and $R^4$ are —CH$_2$CH$_2$CH$_2$—, —CH$_2$CH$_2$CH$_2$CH$_2$—, —CH$_2$C(CH$_3$)$_2$CH$_2$—, —(CH$_2$)$_5$—, —CH=CH—CH=CH—, —CH$_2$COCH$_2$—, —OCH$_2$O—, —OCH$_2$CH$_2$O—, —OCH$_2$CH$_2$CH$_2$O—, —OCH$_2$CH$_2$—, —CH$_2$CH$_2$NH—, —CH=CH—CH=N—, —COCH$_2$CO—, —SCH$_2$CH$_2$—, —SCH$_2$S— and —SCH$_2$CH$_2$S—.

$R^6$ and $R^7$, or $R^7$ and $R^8$ representing a 5- or 6- membered saturated or unsaturated ring is preferably a saturated carbocyclic ring or a saturated ring containing an oxygen atom in the 4-position in the pyridine ring, e.g. —CH$_2$CH$_2$CH$_2$—, —CH$_2$CH$_2$CH$_2$CH$_2$—, —O—CH$_2$CH$_2$—, or —O—CH$_2$CH$_2$CH$_2$—. —A— representing an alkylene group is preferably a lower alkylene group containing 1-7 carbon atoms, especially preferred 1-4 carbon atoms, e.g. methylene, ethylene, propylene or butylene. —A— representing a cycloalkylene group is preferably a lower cycloalkylene containing 3-7 carbon atoms, especially preferred 5 or 6 carbon atoms, e.g. cyclopentylene or cyclohexylene.

Acids suitable for giving acid addition salts of compounds of the formula I are relatively strong acids such as HCl, HBr, HI, HBF$_4$, HPF$_6$, HAuCl$_4$ and HClO$_4$.

Bases suitable for giving alkaline salts of compounds of the formula I are LiOH, NaOH, KOH, Mg(OH)$_2$ and Ca(OH)$_2$.

Preferred groups of the radicals $R^1$, $R^2$, $R^3$ and $R^4$ are hydrogen, alkyl, alkoxy, —CF$_3$, —COOCH$_3$, phenyl, phenoxy, —OCH$_2$O— and —CH$_2$CH$_2$CH$_2$—.

Further preferred groups of the radicals $R^1$, $R^2$, $R^3$ and $R^4$ are hydrogen, methyl, ethyl, isopropyl, CF$_3$.

Preferred groups of the radical $R^5$ is hydrogen and methyl. An especially preferred group of the radical $R^5$ is hydrogen.

Preferred groups of the radicals $R^6$ and $R^8$ are hydrogen, methyl and ethyl.

Preferred groups of the radical $R^7$ are hydrogen, alkyl, alkoxy, aryl, aryloxy, alkenyloxy and cyclic structures with —OCH$_2$CH$_2$— and —OCH$_2$CH$_2$CH$_2$—. Further preferred groups of the radical $R^7$ are hydrogen, methyl, methoxy, phenyl, phenoxy and allyloxy. Particularly preferred are hydrogen, methoxy, phenyl and phenoxy.

Preferred groups of the radical $R^9$ are —CN, —SO$_2^\ominus$, alkylthio, hydroxyalkylthio, carboxyalkylthio, phenylthio. Further preferred groups of the radical $R^9$ are —CN, —SO$_2^\ominus$, ethylthio, t-butylthio, hydroxyethylthio, carboxymethylthio and phenylthio. Still further preferred groups of the radical $R^9$ are ethylthio, hydroxyethylthio and phenylthio.

Preferred of the pyridine fragments are

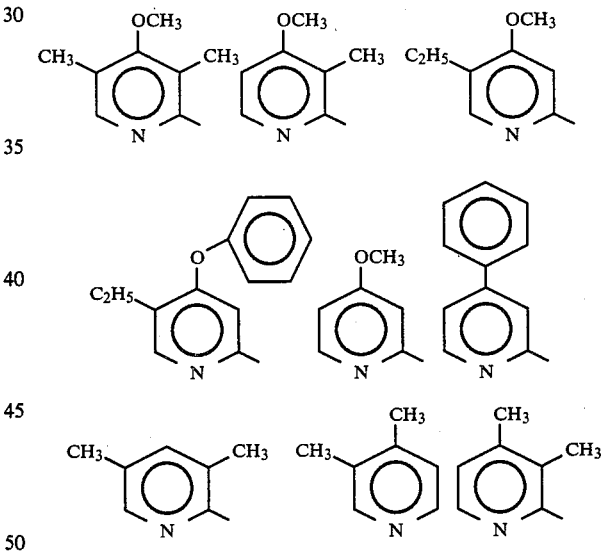

For the compounds with the general formula I containing an unsymmetric centre, e.g. compounds wherein $R^5$ is other than hydrogen, both the pure enantiomers and the racemic mixtures are within the scope of the present invention.

It should be noted that for all the compounds of the invention $R^1$ and $R^4$ as well as $R^2$ and $R^3$ are considered to be equivalent. This is due to the tautomerism in the imidazole part of the benzimidazole nucleus causing an equilibrium between the two possible >NH— forms.

Illustrative examples of compounds included in the scope of the invention are given in the following Table 1.

TABLE 1

Illustrative examples of compounds included in the scope of the invention $$\underset{I}{\begin{array}{c}R^6\\R^7\text{—}\underset{R^8}{\overset{\oplus}{\bigcirc}}\text{—}CH(R^5)\text{—}S\text{—}R^9\\\parallel\\N\text{—}CH=N\text{—}C_6H_3(R^1)(R^2)(R^3)(R^4)\end{array}}\qquad\underset{IA}{\begin{array}{c}R^6\\R^7\text{—}\underset{R^8}{\overset{\oplus}{\bigcirc}}\text{—}CH(R^5)\text{—}S\text{—}R^9\\\parallel\\N\text{—}CH\text{—}NH\,X^{\ominus}\text{—}C_6H_3(R^1)(R^2)(R^3)(R^4)\end{array}}$$

| $R^1$ | $R^2$ | $R^3$ | $R^4$ | $R^5$ | $R^6$ | $R^7$ | $R^8$ | $R^9$ | $I/X^{\ominus}$ |
|---|---|---|---|---|---|---|---|---|---|
| H | H | H | H | H | $CH_3$ | $OCH_3$ | $CH_3$ | $SCH_2CH_2OH$ | I |
| $CH_3$ | $CH_3$ | H | H | H | $CH_3$ | $OCH_3$ | $CH_3$ | $SCH_2CH_2OH$ | I |
| $CH_3$ | $CH_3$ | $CH_3$ | H | H | $CH_3$ | $OCH_3$ | $CH_3$ | $SCH_2CH_2OH$ | I |
| $CH_3$ | $CH_3$ | $CH_3$ | $CH_3$ | H | $CH_3$ | $OCH_3$ | $CH_3$ | $SCH_2CH_2OH$ | I |
| $CH_3$ | H | H | $CH_3$ | H | $CH_3$ | $OCH_3$ | $CH_3$ | $SCH_2CH_2OH$ | I |
| $CH_3$ | H | $CH_3$ | $CH_3$ | H | $CH_3$ | $OCH_3$ | $CH_3$ | $SCH_2CH_2OH$ | I |
| $CH_3$ | $CH_3$ | $CH_3$ | $CH_3$ | H | $CH_3$ | $OCH_3$ | $CH_3$ | $SCH_2CH_2OH$ | I |
| $CH_3$ | $CH_3$ | $CH_3$ | $CH_3$ | H | $CH_3$ | $OCH_3$ | $CH_3$ | $SCH_2CH_2OH$ | I |
| H | $C_2H_5$ | H | H | H | $CH_3$ | $OCH_3$ | $CH_3$ | $SCH_2CH_2OH$ | Cl |
| H | $CH(CH_3)_2$ | H | H | H | $CH_3$ | $OCH_3$ | $CH_3$ | $SCH_2CH_2OH$ | Br |
| H | cyclohexyl | H | H | H | $CH_3$ | $OCH_3$ | $CH_3$ | $SCH_2CH_2OH$ | $BF_4^-$ |
| $CH_3$ | $C_2H_5$ | $CH_3$ | H | H | $CH_3$ | $OCH_3$ | $CH_3$ | $SCH_2CH_2OH$ | $PF_6^-$ |
| H | $OCH_3$ | H | H | H | $CH_3$ | $OCH_3$ | $CH_3$ | $SCH_2CH_2OH$ | $ClO_4^-$ |
| H | $OC_2H_5$ | H | H | H | $CH_3$ | $OCH_3$ | $CH_3$ | $SCH_2CH_2OH$ | I |
| H | Cl | H | H | H | $CH_3$ | $OCH_3$ | $CH_3$ | $SCH_2CH_2OH$ | Cl |
| H | CN | H | H | H | $CH_3$ | $OCH_3$ | $CH_3$ | $SCH_2CH_2OH$ | Br |
| H | $CF_3$ | H | H | H | $CH_3$ | $OCH_3$ | $CH_3$ | $SCH_2CH_2OH$ | I |
| H | $CF_3$ | H | H | H | $CH_3$ | $OCH_3$ | $CH_3$ | $SCH_2CH_2OH$ | $ClO_4^-$ |
| H | $NO_2$ | H | H | H | $CH_3$ | $OCH_3$ | $CH_3$ | $SCH_2CH_2OH$ | I |
| H | $SCH_3$ | H | H | H | $CH_3$ | $OCH_3$ | $CH_3$ | $SCH_2CH_2OH$ | $BF_4^-$ |
| H | $-\underset{\parallel\,O}{S}CH_3$ | H | H | H | $CH_3$ | $OCH_3$ | $CH_3$ | $SCH_2CH_2OH$ | $ClO_4^-$ |

TABLE 1-continued

Illustrative examples of compounds included in the scope of the invention

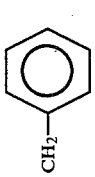

| $R^1$ | $R^2$ | $R^3$ | $R^4$ | $R^5$ | $R^6$ | $R^7$ | $R^8$ | $R^9$ | I/X$^\ominus$ |
|---|---|---|---|---|---|---|---|---|---|
| H | —COOCH$_3$ | H | H | H | CH$_3$ | OCH$_3$ | CH$_3$ | SCH$_2$CH$_2$OH | ClO$_4^-$ |
| H | —COOCH$_3$ | CH$_3$ | H | H | CH$_3$ | OCH$_3$ | CH$_3$ | SCH$_2$CH$_2$OH | ClO$_4^-$ |
| H | —C$_6$H$_5$ | CH$_3$ | H | H | CH$_3$ | OCH$_3$ | CH$_3$ | SCH$_2$CH$_2$OH | ClO$_4^-$ |
| H | —CH$_2$—C$_6$H$_5$ | H | H | H | CH$_3$ | OCH$_3$ | CH$_3$ | SCH$_2$CH$_2$OH | ClO$_4^-$ |
| H | —CH$_2$CH$_2$—C$_6$H$_5$ | H | H | H | CH$_3$ | OCH$_3$ | CH$_3$ | SCH$_2$CH$_2$OH | ClO$_4^-$ |
| H | —O—C$_6$H$_5$ | H | H | H | CH$_3$ | OCH$_3$ | CH$_3$ | SCH$_2$CH$_2$OH | ClO$_4^-$ |

TABLE 1-continued
Illustrative examples of compounds included in the scope of the invention Structures I and IA (pyridinium compounds with substituents $R^1$–$R^9$ and counterion $X^\ominus$).

| $R^1$ | $R^2$ | $R^3$ | $R^4$ | $R^5$ | $R^6$ | $R^7$ | $R^8$ | $R^9$ | I/X$^\ominus$ |
|---|---|---|---|---|---|---|---|---|---|
| H | —OCH$_2$CH$_2$—(phenyl) | H | H | H | CH$_3$ | OCH$_3$ | CH$_3$ | SCH$_2$CH$_2$OH | ClO$_4^-$ |
| H | —O—CO—(phenyl) | H | H | H | CH$_3$ | OCH$_3$ | CH$_3$ | SCH$_2$CH$_2$OH | ClO$_4^-$ |
| H | —COCH$_3$ | H | H | H | CH$_3$ | OCH$_3$ | CH$_3$ | SCH$_2$CH$_2$OH | ClO$_4^-$ |
| H | —COCH$_2$CH$_3$ | H | H | H | CH$_3$ | OCH$_3$ | CH$_3$ | SCH$_2$CH$_2$OH | ClO$_4^-$ |
| H | CH$_3$ | CH$_3$ | H | CH$_3$ | CH$_3$ | H | CH$_3$ | SCH$_2$CH$_2$OH | ClO$_4^-$ |
| H | OCH$_3$ | H | H | CH$_3$ | CH$_3$ | OCH$_3$ | CH$_3$ | SCH$_2$CH$_2$OH | ClO$_4^-$ |
| H | —CH=CH—CH=N— | H | H | H | CH$_3$ | OCH$_3$ | CH$_3$ | SCH$_2$CH$_2$OH | ClO$_4^-$ |
| H | —CH=CH—CH=CH— | H | H | H | CH$_3$ | OCH$_3$ | CH$_3$ | SCH$_2$CH$_2$OH | ClO$_4^-$ |
| H | —CH$_2$CH$_2$CH$_2$— | H | H | H | CH$_3$ | OCH$_3$ | CH$_3$ | SCH$_2$CH$_2$OH | ClO$_4^-$ |
| H | —CH$_2$CH$_2$O— | H | H | H | CH$_3$ | OCH$_3$ | CH$_3$ | SCH$_2$CH$_2$OH | ClO$_4^-$ |
| H | —OCH$_2$O— | H | H | H | CH$_3$ | OCH$_3$ | CH$_3$ | SCH$_2$CH$_2$OH | ClO$_4^-$ |
| H | —CH=CH—CH=C(—)—CH$_2$CH$_2$— | H | H | H | CH$_3$ | OCH$_3$ | CH$_3$ | SCH$_2$CH$_2$OH | ClO$_4^-$ |
| H | OCH$_3$ | H | H | H | CH$_3$ | H | CH$_3$ | SCH$_2$CH$_2$OH | ClO$_4^-$ |
| H | OCH$_3$ | H | H | H | CH$_3$ | CH$_3$ | CH$_3$ | SCH$_2$CH$_2$OH | ClO$_4^-$ |
| H | OCH$_3$ | H | H | H | CH$_3$ | CH$_3$ | H | SCH$_2$CH$_2$OH | ClO$_4^-$ |
| H | OCH$_3$ | H | H | H | H | CH$_3$ | CH$_3$ | SCH$_2$CH$_2$OH | ClO$_4^-$ |

TABLE 1-continued
Illustrative examples of compounds included in the scope of the invention
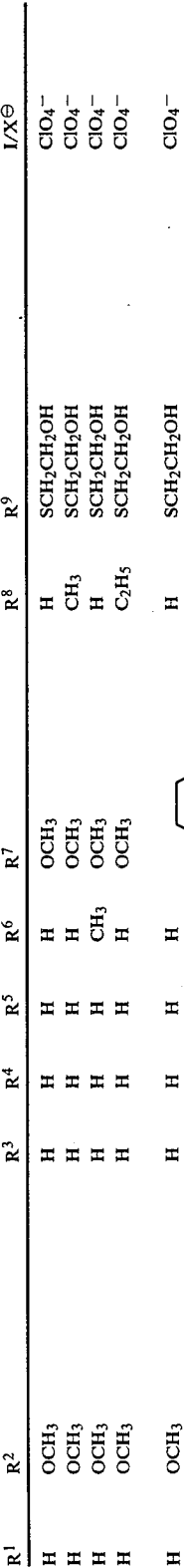
| R1 | R2 | R3 | R4 | R5 | R6 | R7 | R8 | R9 | I/X⊖ |
|---|---|---|---|---|---|---|---|---|---|
| H | OCH3 | H | H | H | H | OCH3 | H | SCH2CH2OH | ClO4− |
| H | OCH3 | H | H | H | CH3 | OCH3 | CH3 | SCH2CH2OH | ClO4− |
| H | OCH3 | H | H | H | H | OCH3 | H | SCH2CH2OH | ClO4− |
| H | OCH3 | H | H | H | H | OCH3 | C2H5 | SCH2CH2OH | ClO4− |
| H | OCH3 | H | H | H | H | ⟨C6H4-CH3⟩ | H | SCH2CH2OH | ClO4− |
| H | OCH3 | H | H | H | H | ⟨C6H5-CH2⟩ | H | SCH2CH2OH | ClO4− |
| H | OCH3 | H | H | H | H | ⟨C6H5-O⟩ | C2H5 | SCH2CH2OH | ClO4− |
| H | OCH3 | H | H | H | H | ⟨C6H5-OCH2⟩ | C2H5 | SCH2CH2OH | ClO4− |

TABLE 1-continued

Illustrative examples of compounds included in the scope of the invention

Structure I:

Pyridinium with substituents R3-R8 on pyridine ring, R5 and S-R9 on exocyclic carbon, linked via N to phenyl ring bearing R1-R4. Counterion I/X⊖.

Structure IA: analogous with N-H X⊖ group.

| R1 | R2 | R3 | R4 | R5 | R6 | R7 | R8 | R9 | I/X⊖ |
|---|---|---|---|---|---|---|---|---|---|
| H | OCH3 | H | H | H | CH3 | OCH2—C6H5 | CH3 | SCH2CH2OH | ClO4⊖ |
| H | OCH3 | H | H | H | CH3 | OCH2CH=CH2 | CH3 | SCH2CH2OH | ClO4⊖ |
| H | OCH3 | H | H | H | CH3 | OCH2C≡CH | CH3 | SCH2CH2OH | ClO4⊖ |
| H | OCH3 | H | H | H | H | —CH=CH—CH=CH— | H | SCH2CH2OH | ClO4⊖ |
| H | OCH3 | H | H | H | H | —CH=CH—CH=CH— | H | SCH2CH2OH | ClO4⊖ |
| H | OCH3 | H | H | H | H | —OCH2CH2— | H | SCH2CH2OH | ClO4⊖ |
| H | OCH3 | H | H | H | H | —CH2CH2CH2O— | H | SCH2CH2OH | ClO4⊖ |
| H | OCH3 | H | H | H | H | —CH2CH2O— | H | SCH2CH2OH | ClO4⊖ |
| H | OCH3 | H | H | H | H | —OCH2CH2— | H | SCH2CH2OH | ClO4⊖ |
| H | OCH3 | H | H | H | CH3 | —CH2CH2CH2— | CH3 | SCH2CH2OH | ClO4⊖ |
| H | OCH3 | H | H | H | CH3 | OCH3 | CH3 | SCH2CH3 | ClO4⊖ |
| H | OCH3 | H | H | H | CH3 | OCH3 | CH3 | S—C6H11 (cyclohexyl) | ClO4⊖ |
| H | OCH3 | H | H | H | CH3 | OCH3 | CH3 | SC(CH3)3 | ClO4⊖ |
| H | OCH3 | H | H | H | CH3 | OCH3 | CH3 | S—C6H5 (phenyl) | ClO4⊖ |

TABLE 1-continued

Illustrative examples of compounds included in the scope of the invention

[Structures I and IA shown: pyridinium-based compounds with substituents R$^5$, R$^6$, R$^7$, R$^8$, R$^9$ on the pyridinium ring and R$^1$, R$^2$, R$^3$, R$^4$ on the phenyl ring, with counterion X$^\ominus$]

| R$^1$ | R$^2$ | R$^3$ | R$^4$ | R$^5$ | R$^6$ | R$^7$ | R$^8$ | R$^9$ | I/X$^\ominus$ |
|---|---|---|---|---|---|---|---|---|---|
| H | OCH$_3$ | H | H | H | CH$_3$ | OCH$_3$ | CH$_3$ | SCH$_2$COOH | ClO$_4^-$ |
| H | OCH$_3$ | H | H | H | CH$_3$ | OCH$_3$ | CH$_3$ | SO$_2^-$ | I |
| H | OCH$_3$ | H | H | H | CH$_3$ | OCH$_3$ | CH$_3$ | —CN | I |
| H | OCH$_3$ | H | H | H | CH$_3$ | OCH$_3$ | CH$_3$ | S—C$_6$H$_4$—Cl (4-) | ClO$_4^-$ |
| H | OCH$_3$ | H | H | H | CH$_3$ | OCH$_3$ | CH$_3$ | S—C$_6$H$_4$—NO$_2$ (4-) | ClO$_4^-$ |

TABLE 1-continued
Illustrative examples of compounds included in the scope of the invention
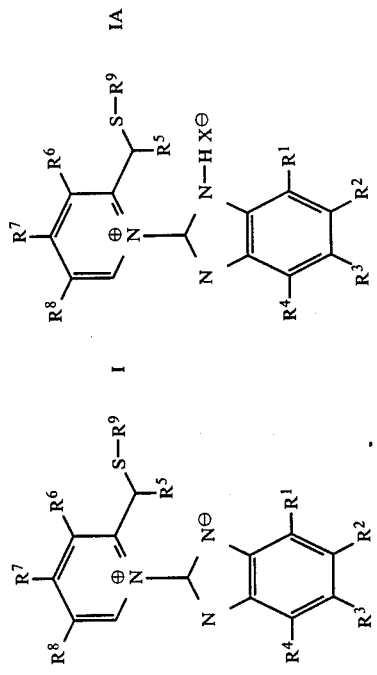
| R¹ | R² | R³ | R⁴ | R⁵ | R⁶ | R⁷ | R⁸ | R⁹ | 1/X⊖ |
|---|---|---|---|---|---|---|---|---|---|
| H | OCH₃ | H | H | H | CH₃ | OCH₃ | CH₃ | | 2 × ClO₄⁻ |

TABLE 1-continued

Illustrative examples of compounds included in the scope of the invention

[Structures shown: two pyridinium compounds with substituents R¹–R⁹, and a third fused structure with OCH₃, CH₃, S, HN, N, CH₃, H₃C groups]

| R¹ | R² | R³ | R⁴ | R⁵ | R⁶ | R⁷ | R⁸ | R⁹ | I/X⊖ |
|---|---|---|---|---|---|---|---|---|---|
| H | CH₃ | CH₃ | H | H | CH₃ | OCH₃ | H | | 2 × Cl⁻ |
| H | COOCH₃ | CH₃ | H | H | CH₃ | H | H | SCH₂CH₂OH | I |
| H | COOCH₃ | CH₃ | H | H | CH₃ | H | H | SCH₂CH₃ | I |
| H | COOCH₃ | CH₃ | H | H | CH₃ | H | H | S-C₆H₅ | Cl⁻ |

TABLE 1-continued

Illustrative examples of compounds included in the scope of the invention

| $R^1$ | $R^2$ | $R^3$ | $R^4$ | $R^5$ | $R^6$ | $R^7$ | $R^8$ | $R^9$ | $I/X^\ominus$ |
|---|---|---|---|---|---|---|---|---|---|
| H | $CH_3$ | H | H | H | $CH_3$ | H | $CH_3$ | $S{-}C_6H_5$ | $Br^-$ |
| H | $CF_3$ | H | H | H | $CH_3$ | $OCH_3$ | $CH_3$ | $S{-}C_6H_5$ | I |
| H | $CF_3$ | H | H | H | $CH_3$ | $OCH_3$ | $CH_3$ | $SCH_2CH_2NH_2$ | I |
| H | $CF_3$ | H | H | H | $CH_3$ | $OCH_3$ | $CH_3$ | $SCH_2CH_2OCCH_3$ (C=O) | I |
| H | $CF_3$ | H | H | H | $CH_3$ | $OCH_3$ | $CH_3$ | $SCH_2{-}C_6H_5$ | $Cl^-$ |
| H | $CF_3$ | H | H | H | H | $OCH_3$ | $CH_3$ | $S{-}C_6H_5$ | $Br^-$ |

TABLE 1-continued

Illustrative examples of compounds included in the scope of the invention

Structure I:
Pyridinium ring with R⁶, R⁷, R⁸ substituents, S—R⁹ group, R⁵, and N⊕ linked to phenyl ring with R¹, R², R³, R⁴

Structure IA:
Similar pyridinium structure with S—R⁹, R⁵, N—H X⊖, and phenyl ring with R¹, R², R³, R⁴

| R¹ | R² | R³ | R⁴ | R⁵ | R⁶ | R⁷ | R⁸ | R⁹ | I/X⊖ |
|---|---|---|---|---|---|---|---|---|---|
| H | CF₃ | H | H | H | H | OCH₃ | CH₃ | cyclohexyl-S | ClO₄⁻ |
| H | CF₃ | H | H | H | H | OCH₃ | CH₃ | SCH₂CH₂N(CH₃)₂ | I |
| H | CF₃ | H | H | H | H | OCH₃ | CH₃ | SCH₂CH₂OH | ClO₄⁻ |
| H | CF₃ | H | H | H | H | OCH₃ | CH₃ | SCH₂CH₂SCH₃ (S=O) | I |
| H | CF₃ | H | H | H | H | OCH₃ | CH₃ | SCH₂C₆H₅O (phenoxy) | Cl⁻ |
| H | CF₃ | H | H | H | H | OCH₃ | CH₃ | S-C₆H₄-NO₂ | Cl⁻ |
| H | CF₃ | H | H | H | H | OCH₃ | CH₃ | SCH₂CH₂OCH₃ | Cl⁻ |
| H | CF₃ | H | H | H | H | OCH₃ | H | SCH₂CH₂SC₂H₅ | I |
| H | CF₃ | H | H | H | H | OCH₃ | H | SCH₂CH₂CN | I |
| H | CF₃ | H | H | H | H | OCH₃ | H | SCH₂COOCH₃ | I |
| H | CF₃ | H | H | H | H | OCH₃ | H | SCH₂CH₂OH | Br⁻ |

TABLE 1-continued
Illustrative examples of compounds included in the scope of the invention
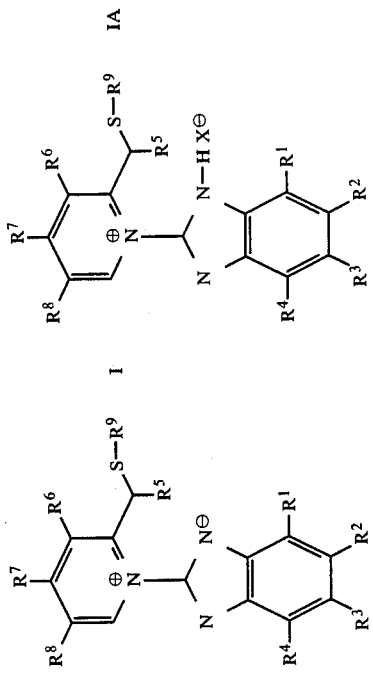
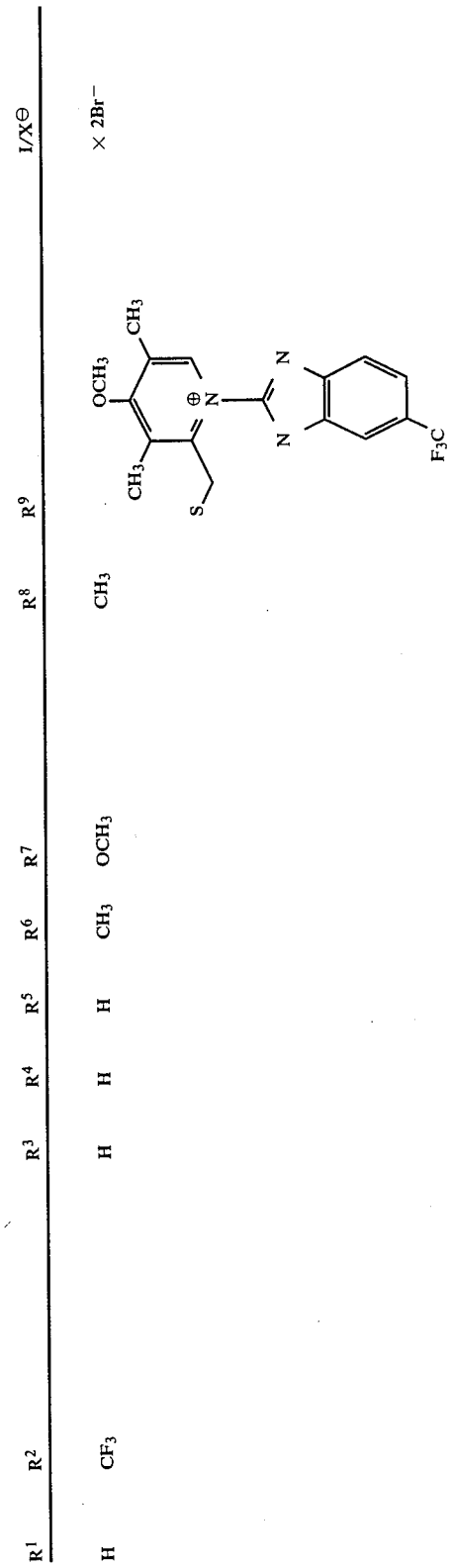
| R[1] | R[2] | R[3] | R[4] | R[5] | R[6] | R[7] | R[8] | R[9] | 1/X[⊖] |
|------|------|------|------|------|------|------|------|------|--------|
| H | CF$_3$ | H | H | H | CH$_3$ | OCH$_3$ | CH$_3$ | | × 2Br$^-$ |

TABLE 1-continued
Illustrative examples of compounds included in the scope of the invention
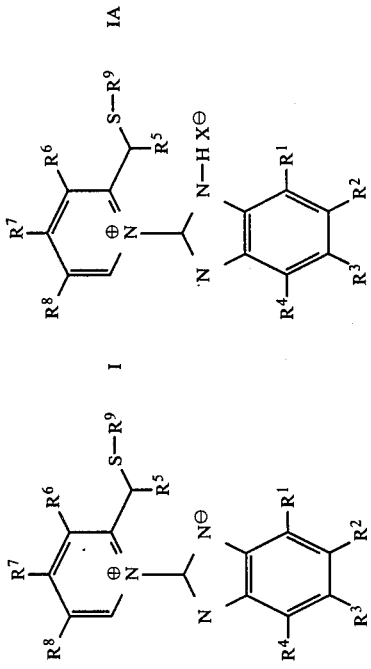
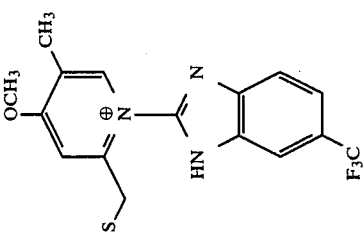
| $R^1$ | $R^2$ | $R^3$ | $R^4$ | $R^5$ | $R^6$ | $R^7$ | $R^8$ | $R^9$ | $I/X^\ominus$ |
|---|---|---|---|---|---|---|---|---|---|
| H | $CF_3$ | H | H | H | H | $OCH_3$ | $CH_3$ | | $2BF_4^-$ |

TABLE 1-continued

Illustrative examples of compounds included in the scope of the invention

| R¹ | R² | R³ | R⁴ | R⁵ | R⁶ | R⁷ | R⁸ | R⁹ | 1/X⊖ |
|---|---|---|---|---|---|---|---|---|---|
| H | CF₃ | H | H | H | H | OCH₃ | H | (OCH₃/F₃C-phenyl pyridinium structure) | 2Cl⁻ |
| CH₃ | OCH₂CH₂OCH₃ | CH₃ | H | H | CH₃ | OCH₃ | CH₃ | SCH₂CH₂OH | ClO₄⁻ |
| H | CH₂CH₂OCH₃ | H | H | H | CH₃ | OCH₃ | CH₃ | SCH₂CH₂OH | ClO₄⁻ |
| H | (o-methylbenzoyl) | H | H | H | CH₃ | OCH₃ | CH₃ | SCH₂CH₂OH | ClO₄⁻ |
| CH₃ | Br | CH₃ | H | H | CH₃ | OCH₃ | CH₃ | SCH₂CH₂OH | ClO₄⁻ |

TABLE 1-continued

Illustrative examples of compounds included in the scope of the invention

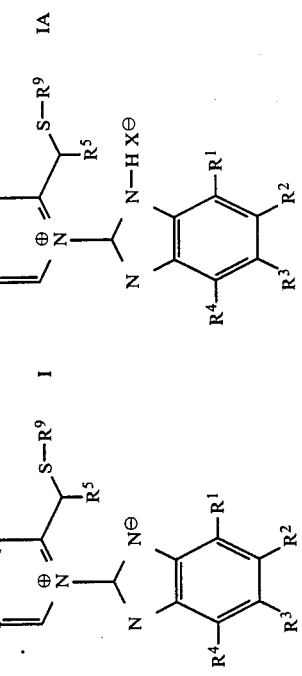

| $R^1$ | $R^2$ | $R^3$ | $R^4$ | $R^5$ | $R^6$ | $R^7$ | $R^8$ | $R^9$ | $I/X^\ominus$ |
|---|---|---|---|---|---|---|---|---|---|
| H | $OCH_3$ | H | H | H | $CH_3$ | $OCH_3$ | $CH_3$ | $SCH_2CH\genfrac{}{}{0pt}{}{COO^-}{\overset{+}{N}H_3}$ | I |
| H | $CH_3$ | H | H | H | $CH_3$ | $CH_3$ | $CH_3$ | $SCH_2CH\genfrac{}{}{0pt}{}{COO^-}{\overset{+}{N}H_3}$ | I |
| H | $CH_3$ | H | H | H | $CH_3$ | H | $CH_3$ | $SCH_2CH\genfrac{}{}{0pt}{}{COO^-}{\overset{+}{N}H_3}$ | $2 \times Cl^-$ |
| H | $CH_3$ | $CH_3$ | H | H | $CH_3$ | $OCH_3$ | $CH_3$ | $SCH_2CH\genfrac{}{}{0pt}{}{COO^-}{\overset{+}{N}H_3}$ | $2 \times Br^-$ |
| H | $CH_3$ | $CH_3$ | H | H | $CH_3$ | $OCH_3$ | H | $SCH_2CH\genfrac{}{}{0pt}{}{COO^-}{\overset{+}{N}H_3}$ | $2 \times ClO_4^-$ |

TABLE 1-continued

Illustrative examples of compounds included in the scope of the invention

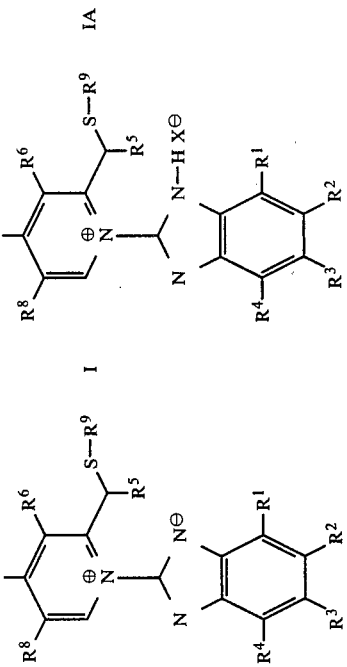      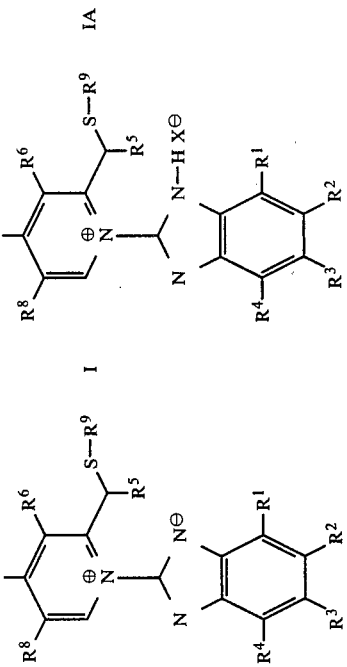

| $R^1$ | $R^2$ | $R^3$ | $R^4$ | $R^5$ | $R^6$ | $R^7$ | $R^8$ | $R^9$ | $I/X^\ominus$ |
|---|---|---|---|---|---|---|---|---|---|
| H | $CH_3$ | H | H | H | H | $OCH_3$ | $C_2H_5$ | $SCH_2CH(COO^-)\overset{+}{N}H_3$ | I |
| H | $CH_3$ | $CH_3$ | H | H | H | $OCH_3$ | $C_2H_5$ | $SCH_2CH(COO^-)\overset{+}{N}H_3$ | I |
| H | $CH_3$ | H | H | H | $CH_3$ | $CH_3$ | H | $SCH_2CH(COO^-)\overset{+}{N}H_3$ | I |
| H | $CH_3$ | H | H | H | H | $CH_3$ | $CH_3$ | $SCH_2CH(COO^-)\overset{+}{N}H_3$ | I |
| H | $CH_3$ | $CH_3$ | H | H | $CH_3$ | $CH_3$ | H | $SCH_2CH(COO^-)\overset{+}{N}H_3$ | I |

TABLE 1-continued

Illustrative examples of compounds included in the scope of the invention

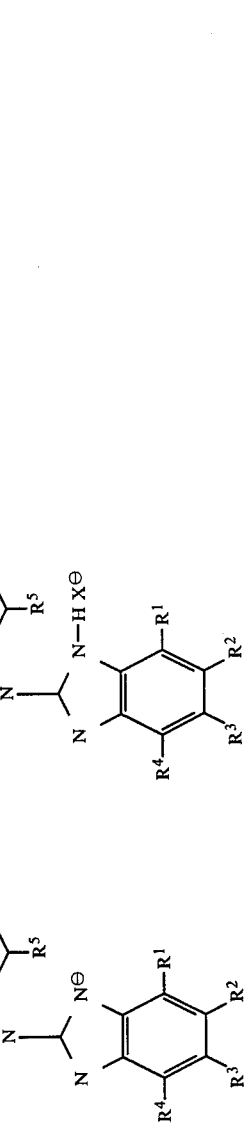

| $R^1$ | $R^2$ | $R^3$ | $R^4$ | $R^5$ | $R^6$ | $R^7$ | $R^8$ | $R^9$ | $I/X^\ominus$ |
|---|---|---|---|---|---|---|---|---|---|
| H | $CH_3$ | $CH_3$ | H | H | $CH_3$ | $CH_3$ | $CH_3$ | $SCH_2CH\begin{smallmatrix}COO^-\\+NH_3\end{smallmatrix}$ | I |
| $CF_3$ | H | H | H | H | $CH_3$ | $OCH_3$ | $CH_3$ | $SCH_2CH\begin{smallmatrix}COO^-\\+NH_3\end{smallmatrix}$ | I |
| $CF_3$ | H | H | H | H | $CH_3$ | $OCH_3$ | H | $SCH_2CH\begin{smallmatrix}COO^-\\+NH_3\end{smallmatrix}$ | I |
| $CF_3$ | H | H | H | H | H | $OCH_3$ | H | $SCH_2CH\begin{smallmatrix}COO^-\\+NH_3\end{smallmatrix}$ | I |
| $CF_3$ | H | H | H | H | H | $OCH_3$ | $CH_3$ | $SCH_2CH\begin{smallmatrix}COO^-\\+NH_3\end{smallmatrix}$ | I |

TABLE 1-continued

Illustrative examples of compounds included in the scope of the invention

| R¹ | R² | R³ | R⁴ | R⁵ | R⁶ | R⁷ | R⁸ | R⁹ | I/X⊖ |
|---|---|---|---|---|---|---|---|---|---|
| H | CF₃ | H | H | H | CH₃ | OCH₃ | CH₃ | SCH₂CH(COO⁻)(⁺NH₃) | I |
| H | CF₃ | H | H | H | CH₃ | OCH₃ | H | SCH₂CH(COO⁻)(⁺NH₃) | |
| H | CF₃ | H | H | H | H | OCH₃ | H | SCH₂CH(COO⁻)(⁺NH₃) | I |
| H | CF₃ | H | H | H | H | OCH₃ | CH₃ | SCH₂CH(COO⁻)(⁺NH₃) | I |
| H | OCH₃ | H | H | H | CH₃ | OCH₃ | CH₃ | SCH₂CH(⁺NH₃)CONHCH₂COO⁻ | I |

TABLE 1-continued

Illustrative examples of compounds included in the scope of the invention

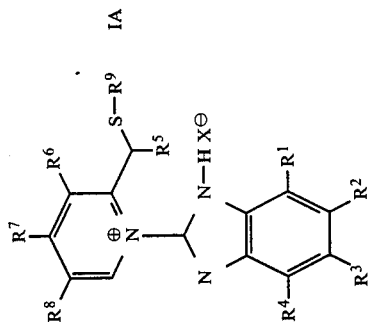

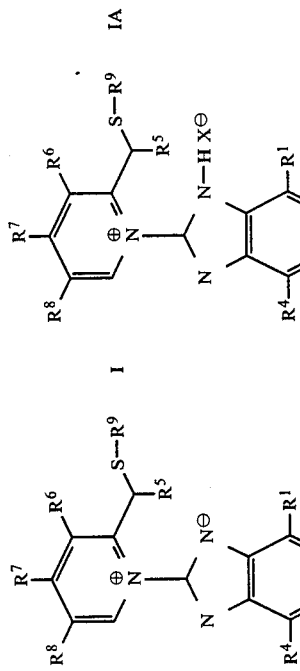

| $R^1$ | $R^2$ | $R^3$ | $R^4$ | $R^5$ | $R^6$ | $R^7$ | $R^8$ | $R^9$ | $I/X^\ominus$ |
|---|---|---|---|---|---|---|---|---|---|
| H | $CH_3$ | H | H | H | $CH_3$ | $OCH_3$ | H | $SCH_2CH\underset{\|}{\overset{\overset{+}{N}H_3}{}}CONHCH_2COO^-$ | $2 \times Cl^-$ |
| $CF_3$ | H | H | H | H | $CH_3$ | $OCH_3$ | H | $SCH_2CH\underset{\|}{\overset{\overset{+}{N}H_3}{}}CONHCH_2COO^-$ | I |
| H | $CF_3$ | H | H | H | $CH_3$ | $OCH_3$ | H | $SCH_2CH\underset{\|}{\overset{\overset{+}{N}H_3}{}}CONHCH_2COO^-$ | I |
| H | $OCH_3$ | H | H | H | $CH_3$ | $OCH_3$ | H | $SCH_2CH\underset{NHCOCH_2CH\underset{\|}{\overset{\overset{+}{N}H_3}{}}COO^-}{\overset{CONHCH_2COOH}{\|}}$ | I |
| H | $CH_3$ | H | H | H | $CH_3$ | $CH_3$ | $CH_3$ | $SCH_2CH\underset{NHCOCH_2CH\underset{\|}{\overset{\overset{+}{N}H_3}{}}COO^-}{\overset{CONHCH_2COOH}{\|}}$ | $2 \times Cl^-$ |

TABLE 1-continued

Illustrative examples of compounds included in the scope of the invention

Structure I:

R⁸—[pyridinium ring with R⁷, R⁶ positions]—CH(R⁵)—S—R⁹ ; N⊖ ; N—[phenyl ring with R¹, R², R³, R⁴]

Structure IA:

R⁸—[pyridinium ring with R⁷, R⁶ positions]—CH(R⁵)—S—R⁹ ; N—H X⊖ ; N—[phenyl ring with R¹, R², R³, R⁴]

| R¹ | R² | R³ | R⁴ | R⁵ | R⁶ | R⁷ | R⁸ | R⁹ | I/X⊖ |
|---|---|---|---|---|---|---|---|---|---|
| H | CH₃ | CH₃ | H | H | CH₃ | OCH₃ | CH₃ | SCH₂CH(CONHCH₂COOH)(NHCOCH₂CH(⁺NH₃)COO⁻) | 2 × Br⁻ |
| H | CH₃ | CH₃ | H | H | CH₃ | OCH₃ | H | SCH₂CH(CONHCH₂COO⁻)(NHCOCH₂CH(⁺NH₃)COO⁻) | I |
| H | CH₃ | H | H | H | H | OCH₃ | C₂H₅ | SCH₂CH(CONHCH₂COO⁻)(NHCOCH₂CH(⁺NH₃)COO⁻) | I |
| H | CH₃ | CH₃ | H | H | H | OCH₃ | C₂H₅ | SCH₂CH(CONHCH₂COO⁻)(NHCOCH₂CH(⁺NH₃)COO⁻) | I |

TABLE 1-continued

Illustrative examples of compounds included in the scope of the invention

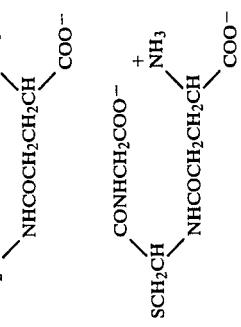   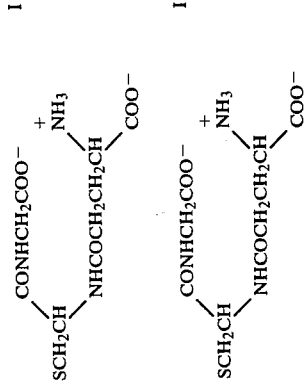

| $R^1$ | $R^2$ | $R^3$ | $R^4$ | $R^5$ | $R^6$ | $R^7$ | $R^8$ | $R^9$ | $I/X^\ominus$ |
|---|---|---|---|---|---|---|---|---|---|
| H | OCH$_3$ | H | H | H | H | OCH$_3$ | C$_2$H$_5$ | SCH$_2$CH(CONHCH$_2$COO$^-$)NHCOCH$_2$CH($\overset{+}{N}$H$_3$)COO$^-$ | I |
| H | OCH$_3$ | H | H | H | H | CH$_3$ | CH$_3$ | SCH$_2$CH(CONHCH$_2$COO$^-$)NHCOCH$_2$CH($\overset{+}{N}$H$_3$)COO$^-$ | I |
| H | OCH$_3$ | H | H | H | CH$_3$ | CH$_3$ | H | SCH$_2$CH(CONHCH$_2$COO$^-$)NHCOCH$_2$CH($\overset{+}{N}$H$_3$)COO$^-$ | I |
| H | CH$_3$ | CH$_3$ | H | H | CH$_3$ | CH$_3$ | CH$_3$ | SCH$_2$CH(CONHCH$_2$COO$^-$)NHCOCH$_2$CH($\overset{+}{N}$H$_3$)COO$^-$ | I |

TABLE 1-continued
Illustrative examples of compounds included in the scope of the invention
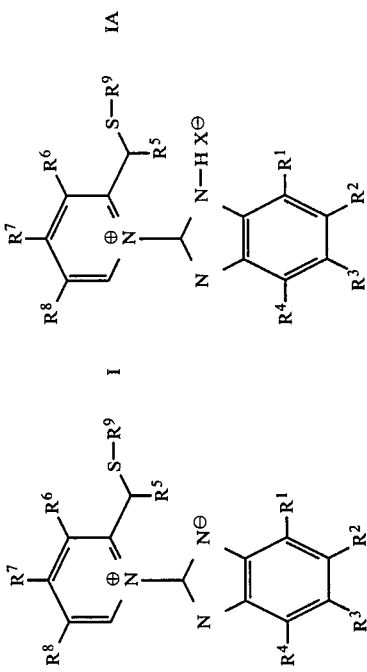
| $R^1$ | $R^2$ | $R^3$ | $R^4$ | $R^5$ | $R^6$ | $R^7$ | $R^8$ | $R^9$ | $I/X^\ominus$ |
|---|---|---|---|---|---|---|---|---|---|
| H | $CH_3$ | H | H | H | $CH_3$ | H | $CH_3$ | 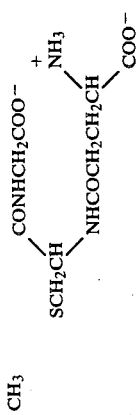 | I |
| $CF_3$ | H | H | H | H | $CH_3$ | $OCH_3$ | H | 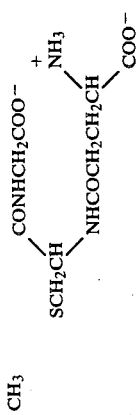 | I |
| $CF_3$ | H | H | H | H | $CH_3$ | $OCH_3$ | $CH_3$ | 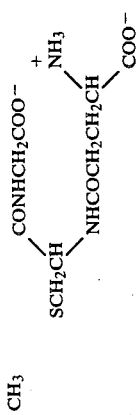 | I |
| $CF_3$ | H | H | H | H | H | $OCH_3$ | $CH_3$ | 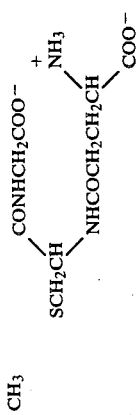 | I |

TABLE 1-continued

Illustrative examples of compounds included in the scope of the invention

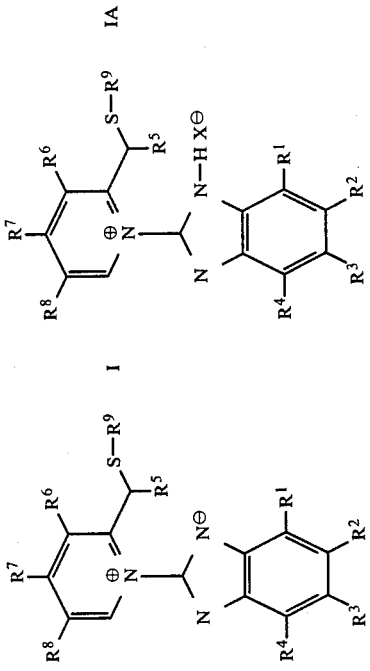

| $R^1$ | $R^2$ | $R^3$ | $R^4$ | $R^5$ | $R^6$ | $R^7$ | $R^8$ | $R^9$ | $I/X^\ominus$ |
|---|---|---|---|---|---|---|---|---|---|
| $CF_3$ | H | H | H | H | H | $OCH_3$ | H | SCH$_2$CH(CONHCH$_2$COO$^-$)(NHCOCH$_2$CH$_2$CH(${}^+$NH$_3$)COO$^-$) | I |
| H | $CF_3$ | H | H | H | H | $OCH_3$ | $CH_3$ | SCH$_2$CH(CONHCH$_2$COO$^-$)(NHCOCH$_2$CH$_2$CH(${}^+$NH$_3$)COO$^-$) | I |
| H | $CF_3$ | H | H | H | $CH_3$ | $OCH_3$ | H | SCH$_2$CH(CONHCH$_2$COO$^-$)(NHCOCH$_2$CH$_2$CH(${}^+$NH$_3$)COO$^-$) | I |
| H | $CF_3$ | H | H | H | $CH_3$ | $OCH_3$ | $CH_3$ | SCH$_2$CH(CONHCH$_2$COO$^-$)(NHCOCH$_2$CH$_2$CH(${}^+$NH$_3$)COO$^-$) | I |

TABLE 1-continued
Illustrative examples of compounds included in the scope of the invention
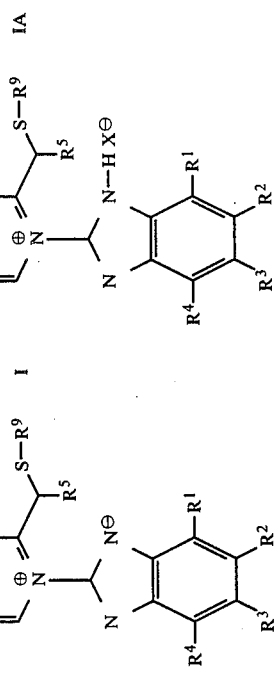
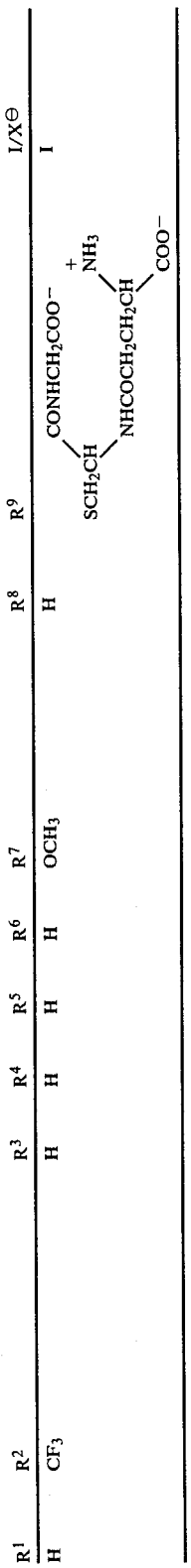
| $R^1$ | $R^2$ | $R^3$ | $R^4$ | $R^5$ | $R^6$ | $R^7$ | $R^8$ | $R^9$ | I/X$^\ominus$ |
|---|---|---|---|---|---|---|---|---|---|
| H | $CF_3$ | H | H | H | H | $OCH_3$ | H | $SCH_2CH\begin{subarray}{l}CONHCH_2COO^-\\NHCOCH_2CH_2CH\begin{subarray}{l}\overset{+}{N}H_3\\COO^-\end{subarray}\end{subarray}$ | I |

PREPARATION

The compounds of formula IA as defined above are prepared by reacting a compound of the formula II

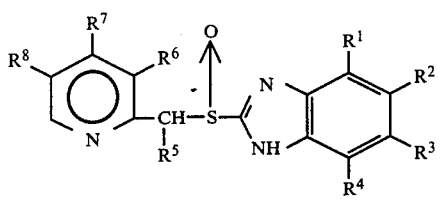

wherein $R^1$, $R^2$, $R^3$, $R^4$, $R^5$, $R^6$, $R^7$ and $R^8$ are as defined above under formula I with a compound of the formula III

wherein $R^9$ is as defined above under formula I, to give a compound of the formula IA. The reaction of a compound of formula II above with a compound of formula III is carried out in the presence of an acid in a suitable solvent. Suitable acids include for example HCl, $HClO_4$, $CF_3COOH$, $HPF_6$, $HBF_4$, HBr. Suitable solvents for the above described reaction include, for example, water, alcohols, preferably lower alkanols such as methanol and ethanol, and halogenated hydrocarbons, such as methylene chloride. If desired a compound of formula IA may be converted to the corresponding compound of formula I by treatment with a base, such as hydroxides, carbonates or hydrocarbonates of alkali metals.

The invention also relates to pharmaceutical compositions containing the new benzimidazole derivatives as active ingredient; to the use of the novel benzimidazole derivatives in therapy, especially for providing gastrointestinal cytoprotective effects in mammals and man; to the use of the novel benzimidazole derivatives in the prevention and treatment of gastrointestinal inflammatory diseases in mammals and man; to a method for inhibiting gastric acid secretion in mammals and man by administering a compound of the formula I; to a method for the treatment of gastrointestinal inflammatory diseases in mammals and man by administering a compound of the formula I; and to a method for providing gastrointestinal cytoprotective effects in mammals and man by administering a compound of the formula I.

For clinical use the compounds of the invention are formulated into pharmaceutical formulations for oral, rectal, parenteral or other mode of administration. The pharmaceutical formulation contains a compound of the invention suitably in combination with a pharmaceutically acceptable carrier. The carrier may be in the form of a solid, semisolid or liquid diluent, or a capsule. These pharmaceutical preparations are a further object of the invention. Usually the amount of active compound is between 0.1–95% by weight of the preparation.

In the preparation of pharmaceutical formulations containing a compound of the present invention in the form of dosage units for oral administration the compound selected may be mixed with a solid, powdered carrier, e.g. calcium phosphate, lactose, saccharose, sorbitol, mannitol, starch, amylopectin, cellulose derivatives or gelatin, as well as with lubricating agents e.g. magnesium stearate, sodium steryl fumarate and polyethylene glycol waxes. The mixture is then processed into granules or pressed into tablets. The tablets may be film coated by a suitable film-forming material.

Soft gelatine capsules may be prepared with capsules containing a mixture of the active compound or compounds of the invention and a suitable vehicle for soft gelatine capsules. Hard gelatine capsules may also contain the active compound in combination with a solid powdered carrier e.g. lactose, saccharose, sorbitol, mannitol, potato starch, corn starch, amylopectin, cellulose derivatives or gelatine.

The oral dosage forms may be enteric coated. The enteric coating is chosen among pharmaceutically acceptable enteric-coating materials e.g. beeswax, shellac or anionic film-forming polymers such as cellulose acetate phthalate, hydroxypropyl methylcellulose phthalate, partly methyl esterified methacrylic acid polymers and the like, if preferred in combination with a suitable plasticizer. To this coating various dyes may be added in order to distinguish among tablets or granules with different active compounds or with different amounts of the active compound present.

The typical daily dose of the active substrate varies within a wide range and will depend on various factors such as for example the individual requirement of each patient, the manner of administration and the disease. In general, oral and parenteral dosages will be in the range of 1 to 400 mg per day of active substance.

The invention is illustrated by the following examples.

EXAMPLE 1

Preparation of 3,5-dimethyl-4-methoxy-2-[(2-hydroxyethyl)dithiomethyl]-1-(5-methoxy-2-benzimidazolyl)-pyridiniumperchlorate 5-Methoxy-2-[[(4-methoxy-3,5-dimethyl-2-pyridinyl)methyl]sulfinyl]-1H-benzimidazole (3.45 g, 0.01 mol) was added under stirring to a solution of mercapto ethanol (0.8 g, 0.011 mol) and $HClO_4$ (1.9 g, 0.013 mol) in 100 ml of $CH_2Cl_2$. A few minutes later 50 ml of $H_2O$ was added. Extraction with $CH_2Cl_2$, separation of the phases, drying of the organic phase and evaporation of the solvent gave the desired product as the $ClO_4^-$ acid salt (4.0 g, 79%), NMR

EXAMPLE 2

Preparation of 3,5-dimethyl-4-methoxy-2[(2-hydroxyethyl)dithiomethyl]-1-(2-benzimidazolyl)pyridiniumhexafluorophosphate 2-[[(4-methoxy-3,5-dimethyl-2-pyridinyl)methyl]sulfinyl]-1H-benzimidazole (0.53 g, 0.0017 mol) was added to 17 ml of 0.1M HCl in methanol and stirred for 7 min. at 37° C. Mercaptoethanol (0.14 g, 0.0018 mol) was added dropwise to the stirred solution. After stirring for 10 min. $HPF_6$ (0.35 ml) in 5 ml of methanol was added. After evaporation of some of the solvent the solution was cooled. The crystallized product was filtered off and suspended in water. After filtration the desired product was obtained as the $PF_6^-$ salt (0.62 g, 70%), NMR

EXAMPLE 3

Preparation of 2-(3,5-dimethyl-4-methoxy-2-thiocyanatomethyl-1-pyridinio)-1-benzimidazolate 5-Methoxy-2-[[(4-methoxy-3,5-dimethyl-2-pyridinyl)methyl]sulfinyl]-1H-benzimidazole (1 g, 0.0029 mol) was added to a solution of KCN (0.57 g, 0.0088 mol) and CF$_3$COOH (1 g, 0.0088 mol) in 100 ml of H$_2$O. To get a clear solution another amount of CF$_3$COOH was added and the mixture was stirred for 30 min. at room-temperature. The solution was made alkaline with NaHCO$_3$. The precipitate was filtered off and suspended in water. Filtration and drying gave the desired product (0.7 g, 68%), NMR

EXAMPLE 22

Preparation of 5-methoxy-2-[3,5-dimethyl-4-methoxy-2-[(2-carboxy-2-aminoethyl-dithiomethyl]-1-pyridinio]-1-benzimidazolate 5-methoxy-2-[[(4-methoxy-3,5-dimethyl-2-pyridinyl)-methyl]sulphinyl]-1H-benzimidazole (1.73 g, 0.005 mol) was added to 50 ml of 0.1 mol HCl in methanol and stirred for 7 minutes at 37° C. Cysteine (0.7 g, 0.0058 mol) was added to the stirred solution. After stirring for 10 minutes HBF$_4$ (35%) (1.5 ml) was added dropwise to the solution. Some of the solvent was evaporated and 50 ml of water was added. The water solution was washed twice with CH$_2$Cl$_2$. The water was evaporated and the desired compound was isolated as a crude material.

The following Table 2 gives data for example 1–21 of compounds of the invention. The compounds according to examples 4–21 were prepared using the same method of preparation as illustrated in examples 1–3.

TABLE 2

Summary of working examples

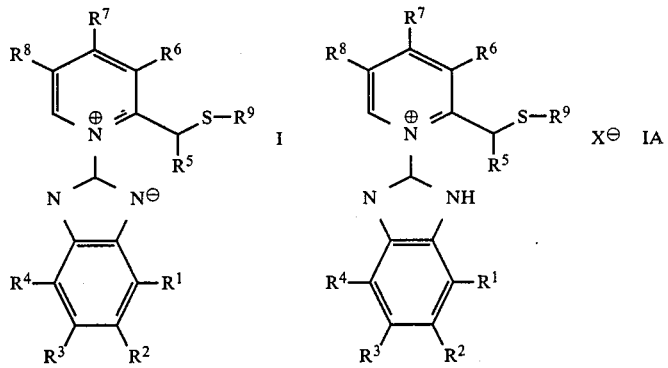

| Ex. | R$^1$ | R$^2$ | R$^3$ | R$^4$ | R$^5$ | R$^6$ | R$^7$ | R$^8$ | R$^9$ | I/X$^\ominus$ | mp (°C.) or other data |
|---|---|---|---|---|---|---|---|---|---|---|---|
| 1 | H | OCH$_3$ | H | H | H | CH$_3$ | OCH$_3$ | CH$_3$ | —SCH$_2$CH$_2$OH | ClO$_4^-$ | NMR |
| 2 | H | H | H | H | H | CH$_3$ | OCH$_3$ | CH$_3$ | —SCH$_2$CH$_2$OH | PF$_6^-$ | NMR |
| 3 | H | OCH$_3$ | H | H | H | CH$_3$ | OCH$_3$ | CH$_3$ | —CN | I | NMR |
| 4 | H | OCH$_3$ | H | H | H | CH$_3$ | OCH$_3$ | CH$_3$ | —SCH$_2$CH$_2$OH | I | NMR |
| 5 | H | OCH$_3$ | H | H | H | CH$_3$ | OCH$_3$ | CH$_3$ | —SCH$_2$CH$_3$ | ClO$_4^-$ | NMR |
| 6 | H | OCH$_3$ | H | H | H | CH$_3$ | OCH$_3$ | CH$_3$ | —S—C$_6$H$_5$ | ClO$_4^-$ | NMR |
| 7 | H | OCH$_3$ | H | H | H | CH$_3$ | OCH$_3$ | CH$_3$ | —SCH$_2$COOH | ClO$_4^-$ | NMR |
| 8 | H | OCH$_3$ | H | H | H | CH$_3$ | OCH$_3$ | CH$_3$ | —SC(CH$_3$)$_3$ | ClO$_4^-$ | NMR |
| 9 | H | OCH$_3$ | H | H | H | CH$_3$ | OCH$_3$ | CH$_3$ | —SO$_2^\ominus$ | I | NMR |
| 10 | H | CH$_3$ | H | H | H | CH$_3$ | OCH$_3$ | CH$_3$ | —SCH$_2$CH$_2$OH | ClO$_4^-$ | NMR |
| 11 | CH$_3$ | H | H | CH$_3$ | H | CH$_3$ | OCH$_3$ | CH$_3$ | —SCH$_2$CH$_2$OH | ClO$_4^-$ | NMR |
| 12 | H | H | H | H | H | CH$_3$ | OCH$_3$ | CH$_3$ | —SCH$_2$CH$_2$OH | ClO$_4^-$ | NMR |
| 13 | H | H | H | H | H | CH$_3$ | OCH$_3$ | CH$_3$ | —SCH$_2$CH$_2$OH | I | NMR |
| 14 | H | H | H | H | H | CH$_3$ | OCH$_3$ | CH$_3$ | —CN | I | NMR |
| 15 | H | CH$_3$ | H | H | H | CH$_3$ | H | CH$_3$ | —SCH$_2$CH$_2$OH | BF$_4^-$ | NMR |
| 16 | H | CH$_3$ | CH$_3$ | H | H | CH$_3$ | H | CH$_3$ | —SCH$_2$CH$_2$OH | BF$_4^-$ | NMR |
| 17 | H | H | H | H | H | H | H | H | —CN | I | NMR |
| 18 | H | CH$_3$ | CH$_3$ | H | H | H | —O—C$_6$H$_5$ | C$_2$H$_5$ | —SCH$_2$CH$_2$OH | ClO$_4^-$ | NMR |
| 19 | H | OCH$_3$ | H | H | H | H | —C$_6$H$_5$ | H | —SCH$_2$CH$_2$OH | BF$_4^-$ | NMR |

TABLE 2-continued

Summary of working examples

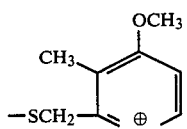

| Ex. | R¹ | R² | R³ | R⁴ | R⁵ | R⁶ | R⁷ | R⁸ | R⁹ | I/X⊖ | mp (°C.) or other data |
|---|---|---|---|---|---|---|---|---|---|---|---|
| 20 | CH₃ | C₂H₅ | CH₃ | H | H | CH₃ | OCH₃ | H | —SCH₂CH₂OH | ClO₄⁻ | NMR |
| 21 | H | CH₃ | CH₃ | H | H | CH₃ | OCH₃ | H | 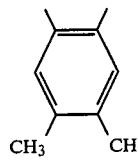 | 2XCl⁻ | NMR |

Identifying data for the compounds according to examples 1–21 are given in the following Table 3.

TABLE 3

| Compound according to example | Solvent | NMR data δ ppm |
|---|---|---|
| 1 | CDCl₃ | 2.5 (t,2H), 2.55 (s,6H), 3.6 (t,2H), 3.9 (s,3H), 4.3 (s,3H), 4.35 (s,2H), 7.1 (dd,1H), 7.15 (d,1H), 7.5 (d,1H), 8.55 (s,1H) |
| 2 | Acetone-d₆ | 2.65 (s,3H), 2.7 (s,3H), 2.75 (t,2H), 3.7 (t,2H), 4.5 (s,3H), 4.75 (s,2H), 7.55–7.75 (m,4H), 9.2 (s,1H) |
| 3 | CDCl₃ | 2.4 (s,3H), 2.55 (s,3H), 3.9 (s,3H), 4.1 (s,3H), 4.8 (s,2H), 6.85 (dd,1H), 7.15 (d,1H), 7.55 (d,1H), 9.5 (s,1H) |
| 4 | CDCl₃ | 2.4 (s,3H), 2.45 (s,3H), 2.5 (t,2H), 3.5 (t,3H), 3.85 (s,3H), 4.05 (s,3H), 4.75 (s,2H), 6.9 (dd,1H), 7.25 (d,1H), 7.65 (d,1H), 8.8 (s,1H) |
| 5 | CDCl₃ | 1.05 (t,3H), 2.4 (q,2H), 2.5 (s,6H), 3.85 (s,3H), 4.25 (s,3H), 4.3 (s,2H), 7.05 (dd,1H), 7.1 (d,1H), 7.65 (d,1H), 8.55 (s,1H) |
| 6 | CDCl₃ | 2.4 (s,6H), 3.9 (s,3H), 4.1 (s,3H), 4.5 (s,2H), 7.0–7.45 (m,7H), 7.65 (d,1H), 8.5 (s,1H) |
| 7 | CDCl₃ | 2.5 (s,3H), 2.55 (s,3H), 3.3 (s,2H), 3.85 (s,3H), 4.3 (s,3H), 4.5 (s,2H), 7.1 (dd,1H), 7.15 (d,1H), 7.65 (d,1H), 8.65 (s,1H), 11.3 (s,1H) |
| 8 | CDCl₃ | 1.1 (s,9H), 2.2 (s,3H), 2.25 (s,3H), 3.9 (s,3H), 4.25 (s,3H), 4.3 (s,2H), 7.15 (dd,1H), 7.2 (s,1H), 7.75 (d,1H), 8.55 (s,1H) |
| 9 | CDCl₃ | 2.4 (s,3H), 2.6 (s,3H), 3.85 (s,3H), 4.4 (s,3H), 4.75 (s,2H), 7.0 (dd,1H), 7.25 (s,1H), 7.5 (bs,1H), 8.5 (s,1H) |
| 10 | CDCl₃ | 2.5 (s,3H), 2.55 (s,6H), 2.6 (t,2H), 3.65 (t,2H), 4.3 (s,3H), 4.35 (s,2H), 7.3 (dd,1H), 7.55 (d,1H), 7.7 (d,1H), 8.5 (s,1H) |
| 11 | CDCl₃ | 2.6 (s,12H), 2.7 (t,2H), 3.65 (t,2H), 4.3 (s,5H), 7.2 (s,2H), 8.55 (s,1H) |
| 12 | CDCl₃ | 2.6 (s,6H), 2.6 (t,2H), 3.6 (t,2H), 4.4 (s,3H), 4.55 (s,2H), 7.4–7.9 (m,4H), 9.05 (s,1H) |
| 13 | CDCl₃ | 2.5 (s,3H), 2.55 (s,3H), 2.55 (t,2H), 3.55 (t,2H), 4.15 (s,3H), 4.75 (s,2H), 7.25–7.4 (m,2H), 7.75–7.9 (m,2H), 8.85 (s,1H) |
| 14 | CDCl₃ | 2.45 (s,3H), 2.5 (s,3H), 4.1 (s,3H), 4.75 (s,2H), 7.0–7.8 (m,4H), 9.4 (s,1H) |
| 15 | CDCl₃ | 2.5 (s,3H), 2.5 (t,2H), 2.6 (s,3H), 2.75 (s,3H), 3.55 (t,2H), 4.4 (s,2H), 7.3 (dd,1H), 7.55 (d,1H), 7.65 (d,1H), 8.35 (d,1H), 8.65 (d,1H) |
| 16 | CDCl₃ | 2.4 (s,6H), 2.5 (t,2H), 2.55 (s,3H), 2.75 (s,3H), 3.55 (t,2H), 4.45 (s,2H), 7.55 (s,2H), 8.35 (d,1H), 8.65 (d,1H) |
| 17 | CDCl₃ | 4.7 (bs,2H), 7.2–7.8 (m,4H), 8.05–8.8 (m,3H), 9.5 (d,1H) |
| 18 | CDCl₃ | 1.4 (t,2H), 2.45 (s,6H), 2.75 (t,2H), 3.05 (q,2H), 3.65 (t,2H), 4.15 (s,2H), 7.3–7.8 (m,8H), 8.6 (s,1H) |

TABLE 3-continued

| Compound according to example | Solvent | NMR data δ ppm |
|---|---|---|
| 19 | CDCl$_3$ | 2.7 (t,2H), 3.8 (t,2H), 3.85 (s,3H), 4.55 (s,2H), 7.1 (dd,1H), 7.15 (d,1H), 7.5–8.0 (m,6H), 8.35 (dd,1H), 8.45 (d,1H), 9.0 (d,1H) |
| 20 | CDCl$_3$ | 1.15 (t,3H), 2.45 (s,3H), 2.5 (s,3H), 2.55 (s,3H), 2.6 (t,2H), 2.8 (q,2H), 3.6 (t,2H), 4.3 (s,3H), 4.35 (s,2H), 7.4 (s,1H), 7.65 (d,1H), 8.75 (d,1H) |
| 21 | acetonitrile-d$_3$ | 2.3 (s,6H), 2.4 (s,12H), 4.2 (s,4H), 4.25 (s,6H), 7.5 (s,4H), 7.55 (d,2H), 8.6 (d,2H) |

Pharmaceutical preparations containing a compound of the invention as active ingredient are illustrated in the following example.

EXAMPLE 23

Tablets 250 g of the compound according to example 1 was mixed with
500 g lactose anhydrous
500 g microcrystalline cellulose
100 g crosslinked polyvinylpyrrolidone
in a mixer. 5 g of magnesium stearate was admixed and the mixture was pressed into tablets each weighing 275 mg.

BIOLOGICAL TESTS

I. In vitro inhibition of gastric H$^+$,K$^+$-ATPase

Hog gastric H$^+$,K$^+$-ATPase was purified according to Saccomani et al., Biochim. Biophys. Acta 465, 311–330, 1977. 10 μg of membrane protein (GI-fraction in the reference listed above) was incubated with 2 mmol/l of piperazine-N,N'bis-(2-ethane sulfonic acid) buffer pH 7.4 and the test compound in concentrations $10^{-7}$–$10^{-4}$M in a final volume of 1 ml. (The test compound was dissolved in methanol. Aliquots of these stock solutions were diluted to a final methanol concentration below 1%, which on its own had no effect on the enzyme activities.) After 30 minutes of incubation, the remaining H$^+$,K$^+$-ATPase activity was determined, according to Wallmark et al., Biochim. Biophys. Acta, 728, 31–38, 1983. A dose-response curve was constructed and the concentration at half-maximal inhibition (IC$_{50}$) could be determined. The test result is given in Table 4 below.

II. Inhibiting effect in vivo on gastric acid secretion in conscious dog

TEST METHOD

Chronic gastric fistula dogs were used. These dogs have been surgically provided with a gastric cannula in the stomach and a duodenal fistula used for direct intraduodenal administration of test compounds. Following a 4 week's recovery period after surgery, tests were performed once a week on each dog. Food and water were withdrawn 18 hours before each test.

The test compound dissolved in 5% ethanol in 0.5% Methocel ® (90 HG, 15.000, Dow Chem Corp.) was administered orally by using a stomach tube. After 1 hour gastric acid secretion was induced by continuous infusion of histamine at individual doses (400–600 nmol/kg, h), resulting in approx. 90% of maximal secretion of gastric acid. The gastric juice was collected by free flow from the gastric cannula in consecutive 30 minutes samples for 2 hours. The samples were titrated to pH 7.0 with 0.1M NaOH using a Radiometer automatic titrator and the acid output was calculated. The percent inhibition of acid secretion was calculated by comparing in each dog the acid output in the test to the acid output in control tests when only the vehicle was given. The peak inhibitory effect for each compound was determined. The test result is given in Table 4 below.

III. In vivo cytoprotective effect: Effect on ethanol-induced gastric lesions in the rat Two groups of female Spraque-Dawley rats (190–220 g) were used, one for the test compound and one for the control experiment. Food, but not water, was removed 24 h before the experiments.

The animals in the test group were treated orally with the test compound dissolved in 10% ethanol in 0.5% Methocel ® immediately before use and the animals in the control group were given the vehicle only in a dose of 2.5 ml/kg.

Thirty minutes later the rats were given orally 1 ml of absolute ethanol (a standard agent for inducing gastric mucosal lesions).

Sixty minutes later the rats were killed by carbon dioxide asphyxiation, their stomachs dissected out and the gastric mucosae were examined for the presence of necrotic lesions. The total lengths of the lesions in the stomachs were measured in the test group and in the control group, in both cases treated thirty minutes before with ethanol. The test result is given in Table 4 below.

The biological tests thus show that the compounds with the general formula I both inhibit gastric acid secretion and have a gastrointestinal cytoprotecting effect.

The ED$_{50}$-value represents the dose of the compound giving 50% reduction of the total lengths of lesions compared to the total lengths of lesions of the control experiment (11.0 cm).

pIC$_{50}$ is the negative logarithm of the concentration (in M) of the test compound giving 50% inhibition.

TABLE 4

| | Biological Effects | | |
|---|---|---|---|
| Example No. | II Dog (μmol/kg) Gast. acid secr. inhib. ED$_{50}$ | III Rat (μmol/kg) Cytoprot. ED$_{50}$ | I Enzyme pIC$_{50}$ |
| 1 | 6 | 15 | 5.0 |
| 6 | 4 | 70 | 6.0 |
| 7 | | 30 | 4.5 |
| 14 | 9 | 20 | |
| 8 | | | 4.5 |
| 5 | | | 4.5 |

We claim:

1. A compound of the formula I

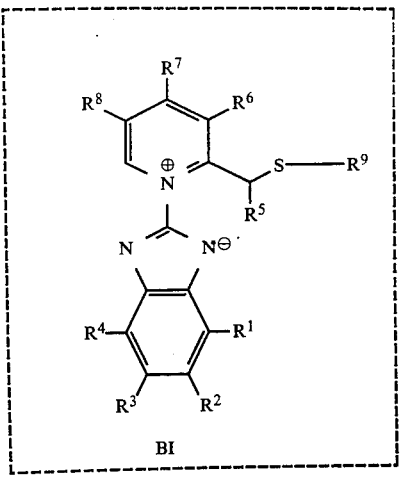

wherein $R^1$, $R^2$, $R^3$ and $R^4$ are the same or different and are hydrogen, alkyl of from 1 to 7 carbon atoms, cycloalkyl of from 3 to 7 carbon atoms, alkoxy of from 1 to 7 carbon atoms, alkoxyalkyl of from 1 to 7 carbon atoms, alkoxyalkoxy of from 1 to 7 carbon atoms in each part, halogen, —CN, —CF$_3$, NO$_2$, —COR$^{12}$, alkylthio containing from 1 to 7 carbon atoms, alkylsulfinyl containing from 1 to 7 carbon atoms, aryl of up to 10 carbon atoms, arylalkyl containing up to 10 carbon atoms in the aryl portion and 1-7 carbon atoms in the alkyl portion, aryloxy of up to 10 carbon atoms, or arylalkoxy containing up to 10 carbon atoms in the aryl portion and 1-7 carbon atoms in the alkyl portion; $R^5$, $R^6$ and $R^8$ are the same or different and are selected from hydrogen an alkyl of 1 to 7 carbon atoms; $R^7$ is hydrogen, alkyl of 1 to 7 carbon atoms, alkoxy of 1 to 7 carbon atoms, aryl of up to 10 carbon atoms, arylalkyl containing up to 10 carbon atoms in the aryl portion and 1-7 carbon atoms in the alkyl portion, aryloxy of up to 10 carbon atoms, arylalkoxy containing up to 10 carbon atoms in the aryl portion and 1-7 carbon atoms in the alkyl portion, alkenyloxy of 2 to 7 carbon atoms or alkynyloxy of 2 to 7 carbon atoms groups; $R^9$ is —CN, SO$_2$H, —SO$_2^\ominus$, —S—A—$R^{10}$, —S—$R^{11}$,

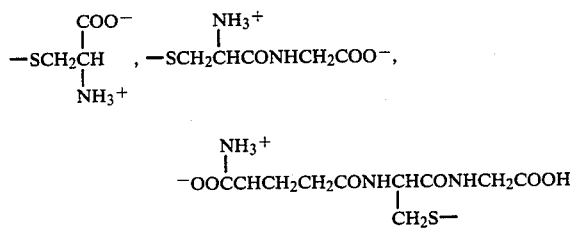

or a group —BI (which is the part of the structure within broken lines as defined in formula I); A is an alkylene of 1 to 7 carbon atoms or cycloalkylene group of 3 to 7 carbon atoms; $R^{10}$ is hydrogen, —CN, —CF$_3$, —NO$_2$, —COR$^{13}$, NR$_2^{14}$, —OR$^{14}$, —SR$^{14}$,

—NHCOR$^{15}$, —OCOR$^{15}$, —SCOR$^{15}$, aryl of up to 10 carbon atoms, arylalkyl containing up to 10 carbon atoms in the aryl portion and 1 to 7 carbon atoms in the alkyl portion, aryloxy of up to 10 carbon atoms or arylalkoxy containing up to 10 carbon atoms in the aryl portion and 1 to 7 carbon atoms in the alkyl portion group; $R^{11}$ is an aryl group of up to 10 carbon atoms which may be optionally substituted by one or more substituents selected from alkyl of 1 to 7 carbon atoms, alkoxy of 1 to 7 carbon atoms, halogen, —CN, —CF$_3$, —NO$_2$ and —COR$^{13}$; $R^{12}$, and $R^{15}$ are the same or different and selected from alkyl of 1 to 7 carbon atoms, aryl of up to 10 carbon atoms, aryloxy of up to 10 carbon atoms and alkoxy of 1 to 7 carbon atoms; $R^{13}$ is selected from alkyl of 1 to 7 carbon atoms, aryl of up to 10 carbon atoms, aryloxy of up to 10 carbon atoms, alkoxy of 1 to 7 carbon atoms and hydroxy; and $R^{14}$ is hydrogen or an alkyl group of 1 to 7 carbon atoms and an acid or alkaline addition salt thereof.

2. A compound according to claim 1, with the general formula IA

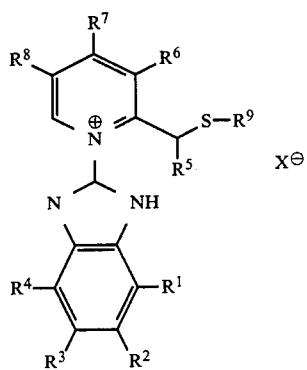

wherein $R^1$ $R^2$, $R^3$, $R^4$, $R^5$, $R^6$, $R^7$, $R^8$, $R^9$ and n are as defined in claim 1 and $X^\ominus$ is Cl$^-$, Br$^-$, I$^-$, BF$^-_4$, PF$^-_6$, AuCl$^-_4$ or ClO$^-_4$.

3. A compound according to claim 1, wherein $R^1$, $R^2$, $R^3$ and $R^4$ are the same or different and are hydrogen, a lower alkyl group having 1-7 carbon atoms, a cycloalkyl group having 3-7 carbon atoms, a lower alkoxy group having 1-7 carbon atoms, an alkoxyalkyl or alkoxyalkoxy group having 1-7 carbon atoms in the alkoxy group and 1-7 carbon atoms in the alkyl or alkoxy group, respectively, chloro, bromo, fluoro, iodo, —CN, —CF$_3$, —NO$_2$, —COR$^{12}$; lower alkylthio having 1-7 carbon atoms, lower alkylsulfinyl having 1-7 carbon atoms, an aryl or aryloxy group having up to 10 carbon atoms, or an arylalkyl or arylalkoxy group each having up to 10 carbon atoms in the aryl group and 1-7 carbon atoms in the alkyl or alkoxy group, respectively; $R^5$, $R^6$ and $R^8$ are the same or different and are selected from hydrogen or lower alkyl having 1-7 carbon atoms; $R^7$ is hydrogen, a lower alkyl or a lower alkoxy group each having 1-7 carbon atoms, an aryl or aryloxy group having up to 10 carbon atoms, an arylalkyl or arylalkoxy group having up to 10 carbon atoms in the aryl group and 1-7 carbon atoms in the alkyl or alkoxy group, respectively, an alkenyloxy or alkynyloxy group having 2-7 carbon atoms; $R^9$ has the definition given in claim 1, wherein A is a lower alkylene group containing 1-7 carbon atoms or a cycloalkylene group containing 3-7 carbon atoms and $R^{10}$ is hydrogen, —CN, —CF$_3$, —NO$_2$, —COR$^{13}$, NR$_2^{14}$, —OR$^{14}$, —SR$^{14}$,

—NHCOR$^{15}$, —OCOR$^{15}$, —SCOR$^{15}$, an aryl or aryloxy group having up to 10 carbon atoms, an arylalkyl or arylalkoxy group having up to 10 carbon atoms in the aryl group and 1-7 carbon atoms in the alkyl or alkoxy group, respectively; R$^{11}$ is an aryl group having up to 10 carbon atoms optionally substituted with one or more substituents selected from lower alkyl having 1-7 carbon atoms, lower alkoxy having 1-7 carbon atoms, chloro, bromo, fluoro, iodo, —CN, —CF$_3$, —NO$_2$ and —COR$^{13}$; and wherein R$^{12}$ and R$^{15}$ are the same and different and are a lower alkyl group or a lower alkoxy group each having 1-7 carbon atoms or an aryl group having up to 10 carbon atoms; R$^{13}$ is a lower alkyl group or a lower alkoxy group each having 1-7 carbon atoms, an aryl group having up to 10 carbon atoms or hydroxy; and R$^{14}$ is hydrogen or a lower alkyl group having 1-7 carbon atoms.

4. A compound according to claim 2, wherein R$^1$, R$^3$, R$^4$ and R$^5$ are hydrogen, R$^2$ and R$^7$ are methoxy, R$^6$ and R$^8$ are methyl, R$^9$ is —SCH$_2$CH$_2$OH and X$^\ominus$ is ClO$_4$.

5. A compound according to claim 2, wherein R$^1$, R$^2$, R$^3$, R$^4$, and R$^5$ are hydrogen, R$^6$ and R$^8$ are methyl, R$^7$ is methoxy, R$^9$ is —SCH$_2$CH$_2$OH, and X$^\ominus$ is PF$_6^-$.

6. A compound according to claim 1, wherein R$^1$, R$^3$, R$^4$ and R$^5$ are hydrogen, R$^2$ and R$^7$ are methoxy, R$^6$ and R$^8$ are methyl and R$^9$ is —CN.

7. A pharmaceutical composition affecting gastric acid secretion and providing gastrointestinal cytoprotective effects containing as active ingredient a therapeutically effective amount of a compound according to claim 1, together with a pharmaceutically acceptable carrier.

8. A method for inhibiting gastric acid secretion comprising administering to mammals including man a compound as defined in claim 1 in an amount effective to inhibit gastric acid secretion.

9. A method for the treatment of gastrointestinal inflammatory diseases in mammals including man comprising administering a compound as defined in claim 1 in a amount effective to treat gastrointestinal inflammatory diseases.

10. A method for providing gastrointestinal cytoprotective effects in mammals including man comprising administering a compound as defined in claim 1 in an amount effective to provide gastrointestinal cytoprotective effects.

* * * * *

UNITED STATES PATENT AND TRADEMARK OFFICE
CERTIFICATE OF CORRECTION

PATENT NO. : 4,689,331  Page 1 of 2

DATED : August 25, 1987

INVENTOR(S) : Ankner et al.

It is certified that error appears in the above-identified patent and that said Letters Patent is hereby corrected as shown below:

<u>First page</u>, part of formula I in the ABSTRACT should be boxed in by broken lines as follows

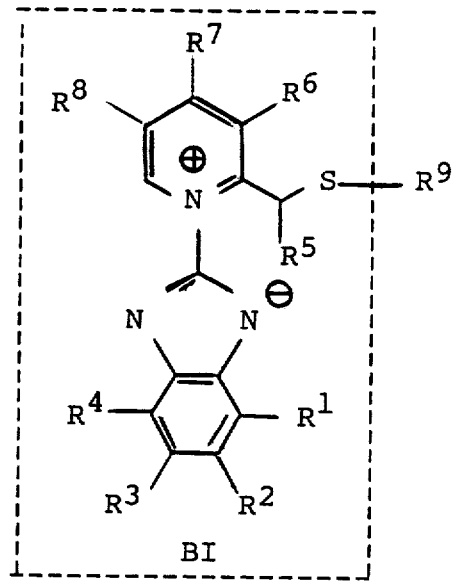

UNITED STATES PATENT AND TRADEMARK OFFICE
CERTIFICATE OF CORRECTION

PATENT NO. : 4,689,331

DATED : August 25, 1987

INVENTOR(S) : Ankner et al.

It is certified that error appears in the above-identified patent and that said Letters Patent is hereby corrected as shown below:

<u>Cols. 1 and 61</u>, $R^9$ should be outside the box formed by the broken line in Formula I as shown above;

<u>Col. 3, line 53</u>, "--A--" should start a new paragraph;

<u>Col. 3, line 57</u>, "--A--" should start a new paragraph;

<u>Col. 4, line 9</u>, "is" should be --are--;

<u>Col. 61, line 33</u>, change "an" to --and--; and

<u>Col. 63, line 10</u>, "the same and different" should read --the same or different--.

Signed and Sealed this

Second Day of February, 1988

Attest:

DONALD J. QUIGG

*Attesting Officer*      *Commissioner of Patents and Trademarks*